United States Patent [19]

Razdan et al.

[11] 3,940,421
[45] Feb. 24, 1976

[54] INTERMEDIATES FOR THE PREPARATION OF THIENOBENZOPYRANS AND THIOPYRANOBENZOPYRANS

[75] Inventors: Raj K. Razdan, Belmont; Harry G. Pars, Lexington, both of Mass.

[73] Assignee: Arthur D. Little, Inc., Cambridge, Mass.

[22] Filed: Sept. 23, 1974

[21] Appl. No.: 508,065

Related U.S. Application Data

[60] Division of Ser. No. 210,170, Dec. 20, 1971, Pat. No. 3,883,551, which is a continuation-in-part of Ser. No. 852,928, Aug. 25, 1969, abandoned.

[52] U.S. Cl. .................. 260/327 TH; 260/332.2 H
[51] Int. Cl.² ........................................ C07D 333/00
[58] Field of Search  260/332.2 H, 327 TH, 343.2 R

[56] References Cited
UNITED STATES PATENTS

| | | | |
|---|---|---|---|
| 2,427,579 | 9/1947 | Stahmann et al. | 260/333 |
| 3,639,426 | 2/1972 | Razdan et al. | 260/343.2 R |

*Primary Examiner*—Henry R. Jiles
*Assistant Examiner*—C. M. S. Jaisle
*Attorney, Agent, or Firm*—Bessie A. Lepper

[57] ABSTRACT

Novel thienobenzopyrans and thiopyranobenzopyrans represented by the formula

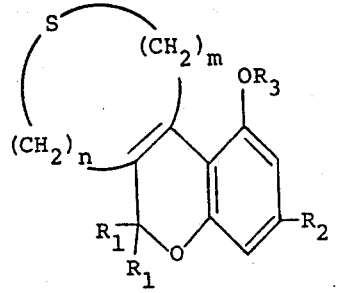

wherein $m$ and $n$ are each 0, 1, 2 or 3 and $m + n$ is 2 or 3; $R_1$ is loweralkyl; $R_2$ is alkyl or cycloalkylloweralkyl and $R_3$ is hydrogen, loweralkyl, loweralkanoyl, carbamyl, N-loweralkylcarbamyl, N,N-diloweralkylcarbamyl, phosphonyl, hemisuccinate or an ester of another such acid, phosphate, dialkylaminoalkyl of the structure

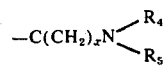

or acid addition salt thereof, or dialkylaminoalkylanoyl of the structure

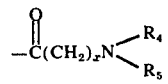

or acid addition salt thereof, wherein $x$ is 1 through 6 and $R_4$ and $R_5$ are loweralkyl; the loweralkyl groups containing from 1 through 6 carbon atoms, the alkyl groups containing from 1 through 20 carbon atoms and the cycloalkyl groups containing from 3 through 8 ring carbon atoms. Novel intermediates for the synthesis of these compounds are also disclosed as well as methods for making the compounds.

12 Claims, No Drawings

INTERMEDIATES FOR THE PREPARATION OF THIENOBENZOPYRANS AND THIOPYRANOBENZOPYRANS

CROSS-REFERENCE TO RELATED APPLICATION

This application is a division of application Ser. No. 210, 170, filed Dec. 20, 1971, now U.S. Pat. No. 3,883,551, issued May 13, 1975, which is a continuation-in-part of copending U.S. Ser. No. 852,928, filed Aug. 25, 1969 now abandoned.

DETAILED DESCRIPTION OF THE INVENTION

This application relates to novel thienobenzopyrans and thiopyranobenzopyrans, to intermediates useful in the preparation thereof and to methods of making and using the novel compounds.

The invention sought to be patented, in a first composition aspect, resides in the concept of a class of chemical compounds which includes more particularly those designated as 7-alkyl(and 7-cycloalkylloweralkyl)-9-hydroxy(and 9-O-esters and 9-O-ethers)-4,4-diloweralkyl-1,2-dihydro-4H-thieno[2,3-c][1]benzopyrans; 7-alkyl(and 7-cycloalkylloweralkyl)-9-hydroxy(and 9-O-esters and 9-O-ethers)-4,4-diloweralkyl-1,3-dihydro-4H-thieno [3,4-c][1]benzopyrans; 7-alkyl(and 7-cycloalkylloweralkyl)-9-hydroxy(and 9-O-esters and 9-O-ethers)-4,4-diloweralkyl-2,3-dihydro-4H-thieno[2,3-c][1]benzopyrans; 8-alkyl(and 8-cycloalkylloweralkyl)-10-hydroxy(and 10-O-esters and 10-O-ethers)-5,5-diloweralkyl-1,2-dihydro-3H,5H-thiopyrano[2,3-c][1]benzopyrans; 8-alkyl(and 8-cycloalkylloweralkyl)-10-hydroxy(and 10-O-esters and 10-O-ethers)-5,5-diloweralkyl-1,2-dihydro-4H,5H-thiopyrano [3,4-c][1]benzopyrans; 8-alkyl(and 8-cycloalkylloweralkyl)-10-hydroxy(and 10-O-esters and 10-O-ethers)-5,5-diloweralkyl-3,4-dihydro-1H,5H-thiopyrano[3,4-c][1]benzopyrans; and 8-alkyl(and 8-cycloalkylloweralkyl)-10-hydroxy(and 10-O-esters and 10-O-ethers)-5,5-diloweralkyl-3,4-dihydro-2H,5H-thiopyrano[2,3-c][1]benzopyrans.

The invention sought to be patented, in a second composition aspect, resides in the concept of a class of chemical compounds which includes more particularly those designated as 7-alkyl(and 7-cycloalkylloweralkyl)-1,2-dihydro-9-hydroxy-4-oxo-4H-thieno[2,3-c][1]benzopyrans; 7-alkyl(and 7-cycloalkylloweralkyl)-1,3-dihydro-9-hydroxy-4-oxo-4H-thieno[3,4-c][1]benzopyrans; 7-alkyl(and 7-cycloalkylloweralkyl)-2,3-dihydro-9-hydroxy-4-oxo-4H-thieno[2,3-c][1]benzopyrans; 8-alkyl(and 8-cycloalkylloweralkyl)-1,2-dihydro-10-hydroxy-5-oxo-3H,5H-thiopyrans[2,3-c][1]benzopyrans; 8-alkyl(and 8-cycloalkylloweralkyl)-1,2-dihydro-10-hydroxy-5-oxo-4H,5H-thiopyrano[3,4-c][1]benzopyrans; 8-alkyl(and 8-cycloalkylloweralkyl)-3,4-dihydro-10-hydroxy-5-oxo-1H,5H-thiopyrano[3,4-c][1]benzopyrans; and 8-alkyl(and 8-cycloalkylloweralkyl)-3,4-dihydro-10-hydroxy-5-oxo-2H,5H-thiopyrano[2,3-c][1]benzopyrans.

The invention sought to be patented in a second composition aspect, resides in the concept of a class of chemical compounds which includes 5-alkyl(and 5-cycloalkylloweralkyl)-2-(4,5-dihydro-2-(2-hydroxy-2-propyl)-thien-3-yl)resorcinols; 5-alkyl(and 5-cycloalkylloweralkyl)-2-(2,5-dihydro-3-(2-hydroxy-2-propyl)-thien-4-yl)resorcinols; 5-alkyl(and 5-cycloalkylloweralkyl)-2-(4,5-dihydro-3-(2-hydroxy-2-propyl)-thien-2-yl)resorcinols; 5-alkyl(and 5-cycloalkylloweralkyl)-2-(4,5-dihydro-2-(2-hydroxy-2-propyl)-6H-thiopyran-3-yl)resorcinols; 5-alkyl(and 5-cycloalkylloweralkyl)-2-(5,6-dihydro-3-(2-hydroxy-2-propyl)-2H-thiopyran-4-yl)resorcinols; 5-alkyl(and 5-cycloalkylloweralkyl)-2-(5,6-dihydro4-(2-hydroxy-2-propyl)-2H-thiopyran-3-yl)resorcinols; and 5-alkyl (and 5-cycloalkylloweralkyl)-2-(4,5-dihydro-3-(2-hydroxy-2-propyl)6H-thiopyran-2-yl)resorcinols.

The tangible embodiments of the first composition aspect of the invention possess the inherent use characteristics of having biological activity as determined by standard pharmacological test procedures for potential therapeutic drugs. The tangible embodiments of the second and third composition aspects of the invention possess the use characteristics of being intermediates in the preparation of the first composition aspect embodiments.

The invention sought to be patented, in its method aspects, resides in the reaction of the appropriate oxo-tetrahydrothiophene-carboxylate or oxo-tetrahydrothiopyrano-carboxylate with an appropriately alkyl(or cycloalkylloweralkyl)-substituted resorcinol to form the intermediates required in the preparation of the desired compounds having biological activity.

It is therefore a primary object of this invention to provide novel chemical compositions of matter, novel intermediates for synthesizing them and methods of forming the chemical compositions and their intermediates. It is another object to provide chemical compositions which exhibit CNS properties. Other objects of the invention will in part be obvious and will in part be apparent hereinafter.

The invention accordingly comprises the several steps and the relation of one or more such steps with respect to each of the others and the composition of matter possessing the characteristics, properties and the relation of components which will be exemplified in the compositions hereinafter described, and the scope of the invention will be indicated in the claims.

Without limiting the generality of the foregoing, illustrative and preferred embodiments of our 7-alkyl(and 7-cycloalkylloweralkyl)-9-hydroxy(and 9-O-esters and 9-O-ethers)-4,4-diloweralkyl-1,2-dihydro-4H-thieno[2,3-c][1]benzopyrans; 7-alkyl(and 7-cycloalkylloweralkyl)-9-hydroxy(and 9-O-esters and 9-O-ethers)-4,4-diloweralkyl-1,3-dihydro-4H-thieno[3,4-c][1]benzopyrans; 7-alkyl(and 7-cycloalkylloweralkyl)-9-hydroxy(and 9-O-esters and 9-O-ethers)-4,4-diloweralkyl-2,3-dihydro-4H-thieno [2,3-c][1]benzopyrans; 8-alkyl(and 8-cycloalkylloweralkyl)-10-hydroxy(and 10-O-esters and 10-O-ethers)-5,5-diloweralkyl-1,2-dihydro-3H,5H-thiopyrano[2,3-c][1]benzopyrans; 8-alkyl(and 8-cycloalkylloweralkyl)-10-hydroxy(and 10-O-esters and 10-O-ethers)-5,5-diloweralkyl-1,2-dihydro-4H,5H-thiopyrano[3,4-c][1]benzopyrans; 8-alkyl(and 8-cycloalkylloweralkyl)-10-hydroxy(and 10-O-esters and 10-O-ethers)-5,5-diloweralkyl-3,4-dihhydro-1H,5H-thiopyrano [3,4-c][1]benzopyrans; and 8-alkyl(and 8-cycloalkylloweralkyl)-10-hydroxy(and 10-O-esters and 10-O-ethers)-5,5-diloweralkyl-3,4-dihydro-2H,5H-thiopyrano[2,3-c][1]benzopyrans are represented by formula I

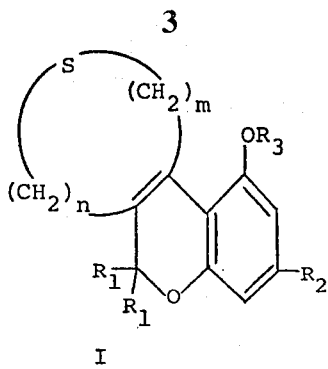

I wherein $m$ and $n$ are each 0, 1, 2 or 3 and $m + n$ is 2 or 3; $R_1$ is loweralkyl; $R_2$ is alkyl or cycloalkylloweralkyl and $R_3$ is hydrogen, loweralkyl, loweralkanoyl, carbamyl, N-loweralkylcarbamyl, N,N-diloweralkylcarbamyl, phosphonyl, hemisuccinate or an ester of another such acid, phosphate, dialkylaminoalkyl of the structure

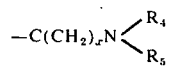

or acid addition salt thereof, or dialkylaminoalkanoyl of the structure

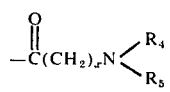

or acid addition salt thereof, wherein $x$ is 1 through 6 and $R_4$ and $R_5$ are loweralkyl; the loweralkyl groups containing from 1 through 6 carbon atoms, the alkyl groups containing from 1 through 20 carbon atoms and the cycloalkyl groups containing from 3 through 8 ring carbon atoms.

Where $m$ is 2 and $n$ is 0, the compounds are represented by the general formula II

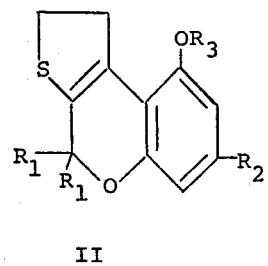

II

Where $m$ is 1 and $n$ is 1, the compounds are represented by general formula III

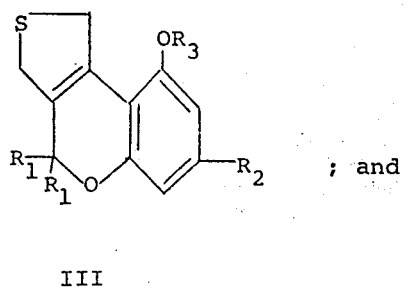

; and

III

Where $m$ is 0 and $n$ is 2, the compounds are represented by general formula IV

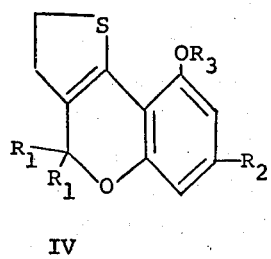

IV

Where $m$ is 3 and $n$ is 0, the compounds are represented by general formula V

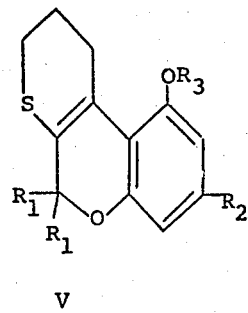

V

Where $m$ is 2 and $n$ is 1, the compounds are represented by general formula VI

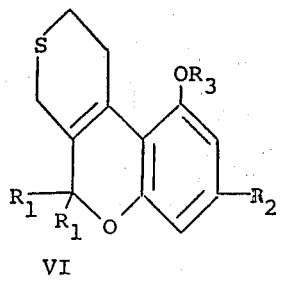

VI

Where $m$ is 1 and $n$ is 2, the compounds are represented by general formula VII

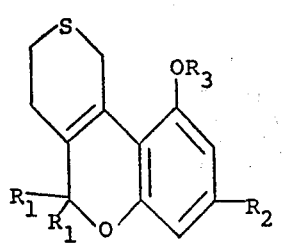

; and

VII

Where $m$ is 0 and $n$ is 3, the compounds are represented by general formula VIII

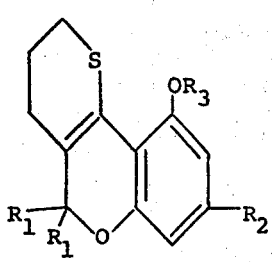

VIII

In formulas II–VIII, $R_1$, $R_2$ and $R_3$ have the same meanings as given for formula I.

Where $R_3$ is dialkylaminoalkyl, the thienobenzopyrans and thiopyranobenzopyrans of this invention may be represented by general formula IX

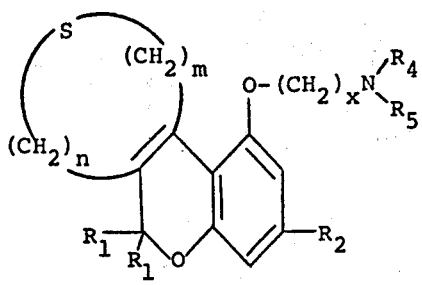

IX where $R_3$ is dialkylaminoalkanoyl, the compounds may be represented by general formula X

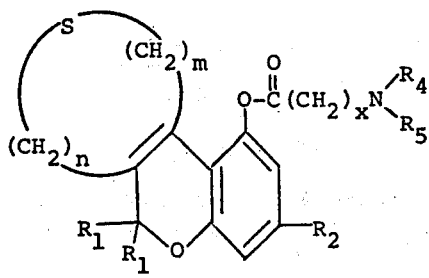

X and the respective acid addition salts of compounds of formulas IX and X may be represented by general formulas XI and XII

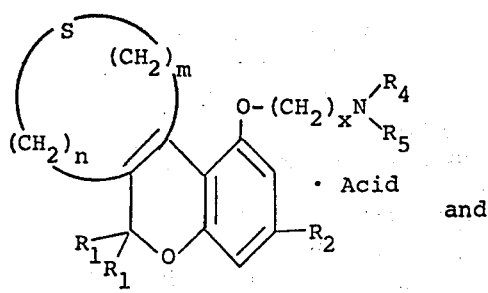 and 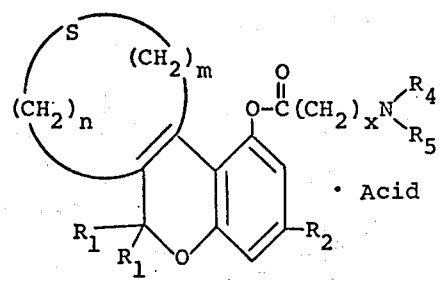

XI  XII where $R_1$ and $R_2$ have the meanings given above, $x$ is a whole number from 1 through 6 and $R_4$ and $R_5$ are loweralkyl.

As used herein, the term "loweralkyl" means saturated, monovalent aliphatic radicals, including straight and branched-chain radicals of from one to six carbon atoms, as illustrated by, but not limited to methyl, ethyl, propyl, isopropyl, butyl, sec.-butyl, amyl, hexyl and the like.

The term "alkyl" means saturated, monovalent aliphatic radicals, including straight and branched-chain radicals of from one to twenty carbon atoms, as illustrated by, but not limited to methyl, n-amyl, n-hexyl, 2-heptyl, n-heptyl, 3-methyl-2-octyl, n-octyl, 2-nonyl, 2-tetradecyl, n-hexadecyl, 2-eicosanyl and the like.

The derivatives of the compounds of formulas I-VIII, where $R_3$ is loweralkyl, loweralkanoyl, carbamyl, N-loweralkylcarbamyl, N,N-diloweralkylcarbamyl or phosphonyl are prepared by reacting the corresponding compound where $R_3$ is hydrogen, preferably in the presence of a basic catalyst, with a loweralkyl halide, to produce the compounds where $R_3$ is lower-alkyl; with a loweralkanoic anhydride (or mixed anhydride) to produce the compounds where $R_3$ is loweralkanoyl; with a molar equivalent of phosgene followed by reaction of the resulting chloroformate with ammonia, a loweralkylamine, or a diloweralkyl amine, to produce the compounds where $R_3$ is, respectively, carbamyl, N-loweralkylcarbamyl or N,N-diloweralkylcarbamyl; or with one molar equivalent amount of phosphorus oxychloride followed by reaction of the resulting dichlorophosphinate with aqueous sodium or potassium carbonate, to produce the compounds where $R_3$ is phosphonyl. Suitable solvents in these synthesis are benzene, toluene, xylene and the like, and suitable basic catalysts are alkali metal carbonates, bicarbonates or hydroxides, dimethylaniline, pyridine and the like.

Where R is dialkylaminoalkyl the compounds, represented by formula IX, may be formed by reacting the appropriate benzopyran with an alkali alkoxide in a solvent, such as ethanol, to give the alkali derivative, which upon treatment with a dialkylaminoalkyl halide in a solvent, such as benzene, results in the formation of the desired derivatives. The acid addition salts of the dialkylaminoalkyl derivatives (formula XI) may be prepared by reacting the free base with an appropriate acid in a suitable organic solvent, in which case the acid salts may be separated directly or obtained by concentration of the solvent.

Where $R_3$ is dialkylaminoalkanoyl (formula X), the appropriate benzopyran is reacted with equimolar amounts of carbodiimide and the appropriate acid or acid salt of the amino group to give either the free base or the acid addition salt (formula XII) directly. If the free base form is obtained, then it may be converted to the acid addition salt in the same manner as described for preparing the acid addition salt of the dialkylaminoalkyl derivative. It is well known that it is possible to convert from one acid addition salt to another by regenerating the free base form and acidifying it.

Appropriate acid addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylene dicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methane sulfonic acid, isethionic acid, benzenesulfonic acid, p-toluene-sulfonic acid, benzenesulfinic acid, butylarsonic acid, diethylphosphinic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The compounds of formula I are prepared by reacting the corresponding oxo-compound of formula XIII

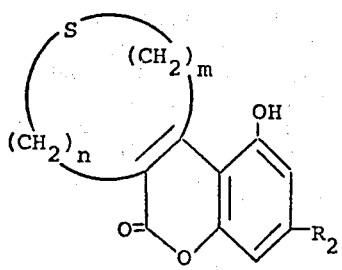

XIII with a loweralkyl magnesium halide as represented by the following reaction

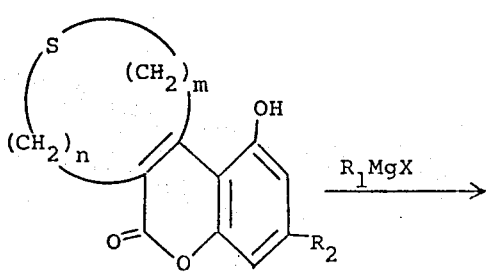

XIII

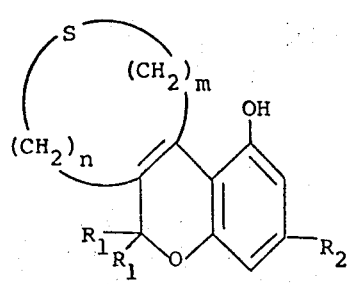

XIV wherein $R_1$ and $R_2$ have the meanings given hereinabove, and $x$ is a halogen. The Grignard reaction is carried out in an organic solvent inert under the conditions of the reaction. Suitable solvents are diethyl ether, dibutyl ether, tetrahydrofuran, anisole, pyridine and the like.

After workup following the Grignard reaction, most of the material is isolated as the triol of formula XIV. This triol is converted to the desired benzopyran by dissolving it in a suitable solvent, such as benzene, and heating to reflux with an acid catalyst, such as p-toluenesulfonic acid, to give the compound of formula XV

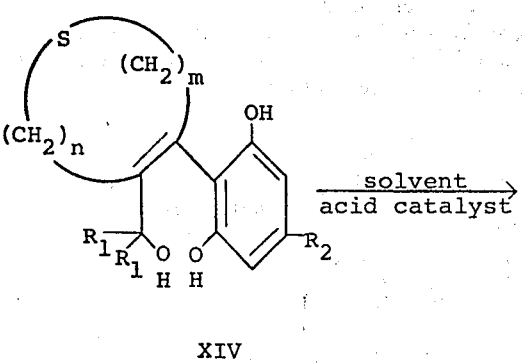

XIV

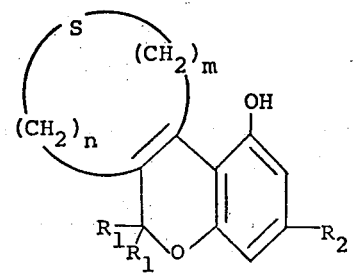

XV

The intermediate which is reacted with the Grignard reagent may be formed by reacting a compound generally defined as

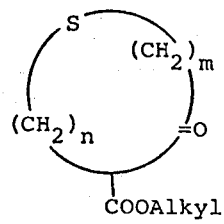

XVI wherein $m$ and $n$ are each 0, 1, 2 or 3 and $m + n$ is 2 or 3, with a 5-alkylresorcinol (or a 5-cycloalkylloweralkylresorcinol).

Where the intermediate takes the form

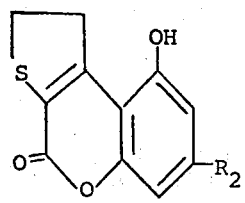

XVII it is prepared by reacting an alkyl 3-oxo-2,3,4,5-tetrahydrothiophene-2-carboxylate of formula XVIII with a resorcinol of formula XIX. The reaction is carried out in the presence of an acid catalyst, such as HCl dissolved in ethanol, and may be represented as as

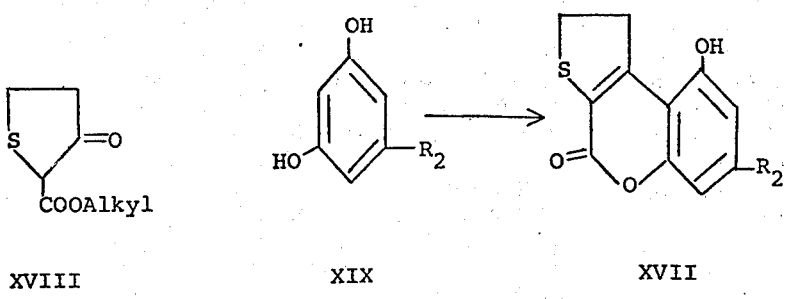

XVIII     XIX     XVII wherein $R_2$ has the meaning previously given.

Where the intermediate takes the form

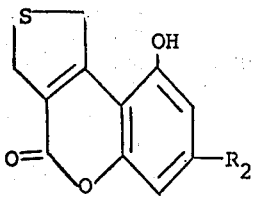

XX it is prepared by reacting an alkyl 4-oxo-2,3,4,5-tetrahydrothiophene-3-carboxylate of formula XXI with a 5-alkylresorcinol (or a 5-cycloalkylloweralkyresorcinol) of formula XIX. The reaction is carried out under conditions similar to those used in forming the compounds of formula XVII by a reaction which may be represented as follows

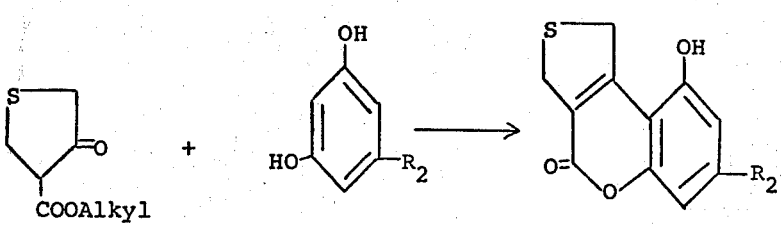

XXI     XIX     XX

Where the intermediate compound to be formed is of the general formula XXII

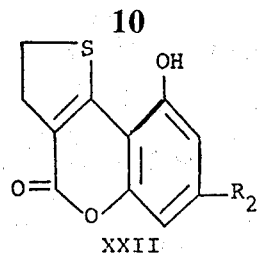

XXII a synthetic route similar to that used for compounds of formulas XVII and XX may be used.

When the intermediate takes the form

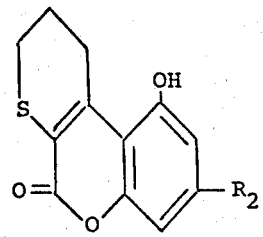

XXIII it can be prepared by reacting an alkyl 3-oxo-2,3,4,5-tetrahydro-6H-thiopyran-2-carboxylate of formula XXIV with a 5-alkylresorcinol of formula XIX under similar conditions described for preparing compounds of formula XVII as illustrated by the reaction

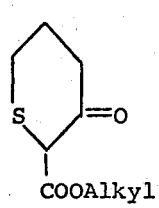 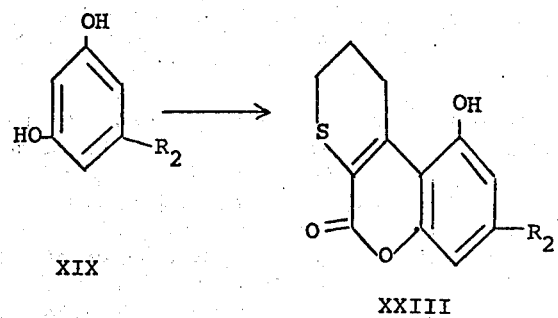

XXIV     XIX     XXIII

Where the intermediate takes the form

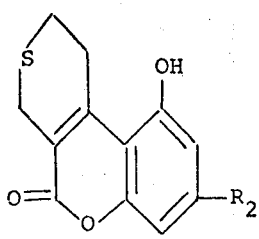

XXV it may be prepared from an alkyl 4-oxo-2,3,4,5-tetrahydro-4H-thiopyran-3-carboxylate as described above.

Where the intermediate compounds to be formed are of the general formulas XXVI and XXVII

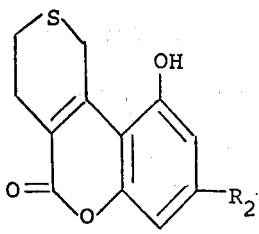

XXVI and

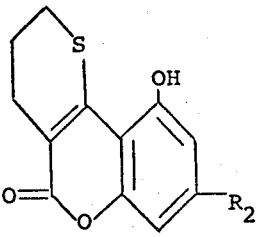

XXVII a synthetic route similar to that used for compounds of formula XXIII may be used.

The intermediates 5-alkyl or 5-cycloalkylloweralkyresorcinols of formula XIX are conveniently prepared by methods generally known in the art, such as by dehydration of a 3,5-diloweralkoxyphenylalkyl (or cycloalkylloweralkyl)carbinol, reduction of the resulting 3,4-diloweralkoxyphenylalkene (or diloweralkoxyphenylcycloalkylloweralkene), and hydriodic acid cleavage of the ether groups to the corresponding 5-alkyl (or 5-cycloalkylloweralkyl)resorcinol. The starting carbinols are in turn prepared by reaction of an appropriate Grignard reagent with a 3,5-diloweralkoxybenzoic acid ester, amide or 3',5'-diloweralkoxyalkanophenone (or 3',5'-diloweralkoxycycloalkyloweralkanophenone).

The intermediate alkyl 3-oxo-2,3,4,5-tetrahydrothiophene-2-carboxylate of formula XVIII and the intermediate alkyl 4-oxo-2,3,4,5-tetrahydrothiophene-3-carboxylate of formula XXI may be prepared by the procedure of Woodward and Eastman, J. Amer. Chem. Soc. 68, 2229 (1946); and the intermediate alkyl 4-oxo-2,3,4,6-tetrahydro-4H-thiopyran-3-carboxylate by the method of G. M. Bennet and L. V. D. Scorah, J. Chem. Soc., 194 (1927). The intermediate alkyl 3-oxo-2,3,4,5-tetrahydro-6H-thiopyran-2-carboxylate can be prepared by the procedure of Leonard and Figueras, J. Amer. Chem. Soc. 74, 917 (1952).

The compounds of formula I exhibit CNS activity and are useful as anti-anxiety agents at dosages of from 0.01 to 20 mg./kg. of body weight daily, and can be used in treating anxiety with or without associated psychoneurotic depressive symptoms.

The anti-depressant activity of the compounds are first established in mice in the modified dopa test described by Everett et al., Fed. Proc., 23, 198 (1964) and confirmed in dogs and monkeys.

The marked tranquilizing activity was established in a battery of standard tests described in *Psychopharmacology, A Ten Year Review*, Public Health Service Publication No. 1836, including overt behavior in mice, rats, dogs and monkeys, blocking fighting response in mice, blocking learning acquisition, etc.

The valium-like profile of both mild anti-depressant and marked tranquilizing activity render the compounds particularly useful as anti-anxiety agents. Like valium, the compounds additionally show sedative hypnotic and anti-convulsant activity.

The compounds exhibit activity when administered either by the oral or intraperitoneal routes, however, the oral route is preferred.

The compounds can be prepared for use by dissolving under sterile conditions in water or in a physiologically compatible aqueous medium such as saline, and stored in ampoules for intramuscular injection. Alternatively, they can be incorporated in unit dosage form as tablets or capsules for oral administration either alone or in combination with suitable adjuvants such as calcium carbonate, starch, lactose, talc, magnesium stearate, gum acacia and the like. Still further the compounds can be formulated for oral administration in aqueous alcohol, glycol or oil solutions or oil-water emulsions in the same manner as conventional medicinal substances are prepared.

The molecular structure of the compounds of our invention were assigned on the basis of study of their infrared (IR), ultraviolet (UV) and nuclear magnetic resonance (NMR) spectra and their transformation products, and confirmed by the correspondence of calculated and found values for the elementary analyses for representative examples.

The following examples will further illustrate the invention without, however, limiting it thereto.

EXAMPLE 1

1,2-Dihydro-9-hydroxy-7-(3-methyl-2-octyl)-4-oxo-4H-thieno[2,3-c][1]benzopyran

A. Methyl 3-oxo-2,3,4,5-tetrahydrothiophene-2-carboxylate

The procedure of Woodward and Eastman (J. Amer. Chem. Soc. 68, 2229 (1946) was followed for the cyclization of 100 g. (0.55 mole) of methyl 3-(methoxycarbonylmethylthio)propionate to give 56 g. (65%) of methyl 3-oxo-2,3,4,5-tetrahydrothiophen-2-carboxylate. NMR spectral analysis showed the product to be a mixture of isomers having the composition of 80% of the desired product

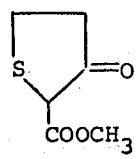

XXVIII and 20% of methyl 4-oxo-2,3,4,5-tetrahydrothiophen-3-carboxylate

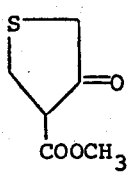

XXIX which could be isolated by fractional distillation.

B. 1,2-Dihydro-9-hydroxy-7-(3-methyl-2-octyl)-4-oxo-4H-thieno[2,3-c][1]benzopyran A solution of 2.5 g. (0.011 mole) of 5-(3-methyl-2-octyl)resorcinol and 2.0 g. (0.013 mole) of the methyl 3-oxo-2, 3,4,5-tetrahydrothiophene-2-carboxylate in 50 ml. of absolute ethanol in a three-necked flask equipped with drying tube was cooled in an ice-water bath and saturated with dry hydrogen chloride. The 5-(3-methyl-2-octyl)resorcinol was prepared according to the method of Adams, MacKenzie and Loewe (J. Amer. Chem. Soc. 70, 664–8 (1948)). The reaction mixture was allowed to stand for three days at room temperature, during which time a heavy yellow solid formed. The hydrogen chloride was evaporated, the mixture was concentrated and the solid was filtered and washed with ethanol. The yield of the crude benzopyrone thus obtained was 2.6 g. (59%), m.p. 190°–205°C.

Repeated crystallization from absolute ethanol gave an analytical sample, m.p. 209°–212°C, of the compound XXX

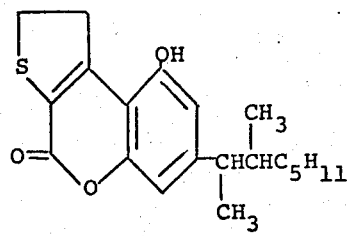

XXX

Anal. Calcd. for $C_{20}H_{26}O_3S$: C, 69.36; H, 7.51; S, 9.25; Found: C, 69.15; H, 7.41; S, 9.30

EXAMPLE 2

1,2-Dihydro-9-hydroxy-7-methyl-4-oxo-4H-thieno[2,3-c][1]benzopyran

Following the procedure similar to that described in Example 1B hereinabove, methyl 3-oxo-2,3,4,5-tetrahydrothiophene-2-carboxylate is reacted with 5-methylresorcinol to give 1,2-dihydro-9-hydroxy-7-methyl-4-oxo-4H-thieno[2,3-c][1]benzopyran.

EXAMPLE 3

1,2-Dihydro-7-(2-heptyl)-9-hydroxy-4-oxo-4H-thieno[2,3-c][1]benzopyran

Following a procedure similar to that described in Example 1B hereinabove, methyl 3-oxo-2,3,4,5-tetrahydrothiophene-2-carboxylate is reacted with 5-(2-heptyl)resorcinol to give 1,2-dihydro-7-(2-heptyl)-9-hydroxy-4-oxo-4H-thieno[2,3-c][1]benzopyran.

EXAMPLE 4

7-(3-Cyclopropyl-2-propyl)-1,2-dihydro-9-hydroxy-4-oxo-4H-thieno[2,3-c][1]benzopyran Following a procedure similar to that described in Example 1B hereinabove, methyl 3-oxo-2,3,4,5-tetrahydrothiophene-2-carboxylate is reacted with 5-(3-cyclopropyl-2-propyl)resorcinol to give 7-(3-cyclopropyl-2-propyl)-1,2-dihydro-9-hydroxy-4-oxo-4H-thieno[2,3-c][1]benzopyran.

EXAMPLE 5

1,2-Dihydro-9-hydroxy-4-oxo-7-(1-pentyl)-4H-thieno[2,3-c][1]benzopyran

Following a procedure similar to that described in Example 1B hereinabove, methyl 3-oxo-2,3,4,5-tetrahydrothiophene-2-carboxylate is reacted with 5-(1-pentyl)resorcinol to give 1,2-dihydro-9-hydroxy-4-oxo-7-(1-pentyl)-4H-thieno[2,3-c][1]benzopyran.

EXAMPLE 6

7-(1-Cyclohexylethyl)-1,2-dihydro-9-hydroxy-4-oxo-4H-thieno[2,3-c][1]benzopyran

Following a procedure similar to that described in Example 1B hereinabove, methyl 3-oxo-2,3,4,5-tetrahydrothiophene-2-carboxylate is reacted with 5-(1-cyclohexylethyl)resorcinol to give 7-(1-cyclohexylethyl)-1,2-dihydro-9-hydroxy-4-oxo-4H-thieno[2,3-c][1]benzopyran.

EXAMPLE 7

1,2-Dihydro-7-(2-eicosyl)-9-hydroxy-4-oxo-4H-thieno[2,3-c][1]benzopyran

Following a procedure similar to that described in Example 1B hereinabove, methyl 3-oxo-2,3,4,5-tetrahydrothiophene-2-carboxylate is reacted with 5-(2-eicosyl)resorcinol to give 1,2-dihydro-7-(2-eicosyl)-9-hydroxy-4-oxo-4H-thieno-[2,3-c][1]benzopyran.

EXAMPLE 8

1,2-Dihydro-4,4-dimethyl-9-hydroxy-7-(3-methyl-2-octyl)-4H-thieno[2,3-c][1]benzopyran The Grignard reagent was prepared by bubbling bromomethane into a mixture of 7.2 g. (0.3 mole) of magnesium turnings in ether. When all the magnesium had reacted, the solution was refluxed for a short time to remove the excess bromomethane. A solution of 9.0 g. (0.026 mole) of 1,2-dihydro-9-hydroxy-7-(3-methyl-2-octyl)-4-oxo-4H-thieno[2,3-c][1]benzopyran in 250 ml. of benzene was added to the methylmagnesium bromide and the reaction mixture was kept at 45°C for 24 hours. After the addition of saturated ammonium chloride, the benzene/ether layer was separated, and the aqueous layer was extracted with ether. The combined organic layers were washed with water, dried over sodium sulfate and evaporated to give a greenish, gummy residue. The material was shown to be pure by thin-layer chromatography (TLC) (10% MeOH/CHCl₃); and the IR and NMR spectra indicated the compound to be 5-(3-methyl-2-octyl)-2-(4,5-dihydro-2-(2-hydroxy-2-propyl)thien-3-yl)resorcinol (triol).

2.0 g. of the triol was dissolved in benzene and refluxed for 3 hours in the presence of a small amount of p-toluenesulfonic acid. The benzene solution was concentrated and the residue was chromatographed using Florisil column support, 60-100 mesh, and graded ether/petroleum ether solvent mixtures. The IR, UV and NMR spectra confirmed the structure

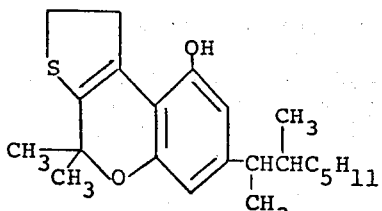

XXXI

Anal. Calcd. for $C_{22}H_{32}O_2S$: C, 73,33; H, 8.91; S, 8.91; Found: C, 73, 10; H, 9.16; S, 8.75

The gum exhibited $\lambda_{max}^{EtOH}$ 320 m$\mu$ (log$\epsilon$ 3.951). IR, UV and NMR spectra confirmed the pyran structure.

EXAMPLE 9

1,2-Dihydro-9-hydroxy-4,4,7-trimethyl-4H-thieno[2,3-c][1]benzopyran

Following the procedure similar to that described in Example 8 hereinabove, 1,2-dihydro-9-hydroxy-7-methyl-4-oxo-4H-thieno[2,3-c][1]benzopyran is reacted with methylmagnesium bromide to give 1,2-dihydro-9-hydroxy-4,4,7-trimethyl-4H-thieno-[2,3-c][1]benzopyran.

EXAMPLE 10

1,2-Dihydro-4,4-dimethyl-7-(2-heptyl)-9-hydroxy-4H-thieno[2,3-c][1]benzopyran

By reacting 1,2-dihydro-7-(2-heptyl)-9-hydroxy-4-oxo-4H-thieno[2,3-c][1]benzopyran with methylmagnesium bromide in a procedure similar to that described hereinabove in Example 8 there is obtained 1,2-dihydro-4,4-dimethyl-7-(2-heptyl)-9-hydroxy-4H-thieno[2,3-c][1]benzopyran.

EXAMPLE 11

7-(3-Cyclopropyl-2-propyl)-4,4-dimethyl-1,2-dihydro-9-hydroxy-4H-thieno[2,3-c][1]benzopyran 7-(3-cyclopropyl-2-propyl)-1,2-dihydro-9-hydroxy-4-oxo-4H-thieno[2,3-c][1]benzopyran is reacted with methylmagnesium bromide in a procedure similar to that described hereinabove in Example 8 to give 7-(3-cyclopropyl-2-propyl)-4,4-dimethyl-1,2-dihydro-9-hydroxy-4H-thieno[2,3-c][1]benzopyran.

EXAMPLE 12

1,2-dihydro-4,4-dimethyl-9-hydroxy-7-(1-pentyl)-4H-thieno[2,3-c][1]benzopyran 1,2-Dihydro-9-hydroxy-4-oxo-7-(1-pentyl)-4H-thieno[2,3-c][1]benzopyran is reacted with methylmagnesium bromide in a procedure similar to that described hereinabove in Example 8 to give 1,2-dihydro-4,4-dimethyl-9-hydroxy-7-(1-pentyl)-4H-thieno[2,3-c][1]benzopyran.

EXAMPLE 13

7-(1-Cyclohexylethyl)-1,2-dihydro-4,4-dimethyl-9-hydroxy-4H-thieno[2,3-c][1]benzopyran 7-(1-Cyclohexylethyl)-1,2-dihydro-9-hydroxy-4-oxo-4H-thieno[2,3-c][1]benzopyran is reacted with methylmagnesium bromide according to the procedure described hereinabove in Example 8 to give 7-(1-cyclohexylethyl)-1,2-dihydro-4,4-dimethyl-9-hydroxy-4H-thieno[2,3-c][1-]benzopyran.

EXAMPLE 14

1,2-Dihydro-4,4-dimethyl-7-(2-eicosyl)-9-hydroxy-4H-thieno[2,3-c][1]benzopyran 1,2-Dihydro-7-(2-eicosyl)-9-hydroxy-4-oxo-4H-thieno-[2,3-c][1]benzopyran is reacted with methylmagnesium bromide according to the procedure described hereinabove in Example 8 to give 1,2-dihydro-4,4-dimethyl-7-(2-eicosyl)-9-hydroxy-4H-thieno[2,3-c][1]benzopyran.

EXAMPLE 15

4,4-Di(1-hexyl)-1,2-dihydro-9-hydroxy-7-methyl-4H-thieno[2,3-c][1]benzopyran

By reacting 1,2-dihydro-9-hydroxy-7-methyl-4-oxo-4H-thieno[2,3-c][1]benzopyran with n-hexyl magnesium bromide, using the manipulative procedure described in Example 8, there is obtained 4,4-di(1-hexyl)-1,2-dihydro-9-hydroxy-7-methyl-4H-thieno[2,3-c][1]benzopyran.

EXAMPLE 16

7,(3-Cyclopropyl-2-propyl)-4,4-di(1-hexyl)-1,2-dihydro-9-hydroxy-4H-thieno[2,3-c][1]benzopyran By reacting 7-(3-cyclopropyl-2-propyl)-1,2-dihydro-9-hydroxy-4-oxo-4H-thieno[2,3-c][1]benzopyran with n-hexylmagnesium bromide, using the manipulative procedure described above in Example 8, there is obtained 7-(3-cyclopropyl-2-propyl)-4,4-di(1-hexyl)-1,2-dihydro-9-hydroxy-4H-thieno[2,3-c][1]benzopyran.

EXAMPLE 17

4,4-Di(1-hexyl)-,2-dihydro-9-hydroxy-7-(3-methyl-2-octyl)-4H-thieno[2,3-c][1]benzopyran By reacting 1,2-dihydro-9-hydroxy-7-(3-methyl-2-octyl)-4-oxo-4H-thieno[2,3-c][1]benzopyran with n-hexylmagnesium bromide, using the manipulative procedure described in Example 8, there is obtained 4,4-di(1-hexyl)-1,2-dihydro-9-hydroxy-7-(3-methyl-2-octyl)-4H-thieno[2,3-c][1]benzopyran.

EXAMPLE 18

9-Acetoxy-1,2-dihydro-4,4-dimethyl-7-(3-methyl-2-octyl)-4H-thieno[2,3-c][1]benzopyran By reacting 1,2-dihydro-4,4-dimethyl-9-hydroxy-7-(3-methyl-2-octyl)-4H-thieno[2,3-c][1]benzopyran with acetic anhydride, there is obtained 9-acetoxy-1,2-dihydro-4,4-dimethyl-7-(3-methyl-2-octyl)-4H-thieno[2,3-c][1]benzopyran.

EXAMPLE 19

1,2-Dihydro-4,4-dimethyl-9-methoxy-7-(3-methyl-2-octyl-4H-thieno[2,3-c][1]benzopyran By reacting 1,2-dihydro-4,4-dimethyl-9-hydroxy-7-(3-methyl-2-octyl)-4H-thieno[2,3-c][1]benzopyran with methyl iodide in the presence of sodium ethoxide, there is obtained 1,2-dihydro-4,4-dimethyl-9-methoxy-7-(3-methyl-2-octyl)-4H-thieno[2,3-c][1]benzopyran.

EXAMPLE 20

9-Carbamyloxy-1,2-dihydro-4,4-dimethyl-7-(3-methyl-2-octyl)-4H-thieno[2,3-c][1]benzopyran A benzene solution of equimolar quantities of 1,2-dihydro-4,4-dimethyl-9-hydroxy-7-(3-methyl-2-octyl)-4H-thieno[2,3-c][1]benzopyran, phosgene and dimethylaniline is stirred at room temperature for 24 hours. The reaction mixture is evaporated to dryness and the residue is triturated with ether. The solid which forms is separated by filtration and the filtrate is evaporated to give the chloroformyl derivative. By reacting the chloroformate with liquid ammonia, there is obtained 9-carbamyloxy-1,2-dihydro-4,4-dimethyl-7-(3-methyl-2-octyl)-4H-thieno[2,3-c][1]benzopyran.

EXAMPLE 21

1,2-Dihydro-4,4-dimethyl9-(N-methylcarbamyloxy)-7-(3-methyl-2-octyl)-4H-thieno[2,3-c][1]benzopyran By reacting 1,2-dihydro-4,4-dimethyl-9-hydroxy-7-(3-methyl-2-octyl)-4H-thieno[2,3-c][1]benzopyran with an equimolar amount of phosgene in the presence of dimethylaniline in a procedure similar to that described in Example 20 and reacting the resulting chloroformate with methylamine, there is obtained 1,2-dihydro-4,4-dimethyl-9-(N-methylcarbamyloxy)-7-(3-methyl-2-octyl)-4H-thieno[2,3-c][1]benzopyran.

EXAMPLE 22

1,2-Dihydro-4,4-dimethyl-9-(N,N-dimethylcarbamyloxy)-7-(3-methyl-2-octyl)-4H-thieno[2,3-c][1]benzopyran By reacting 1,2-dihydro-4,4-dimethyl-9-hydroxy-7-(3-methyl-2-octyl)-4H-thieno[2,3-c][1]benzopyran with an equimolar amount of phosgene in the presence of dimethylaniline in a procedure similar to that described above in Example 20 and reacting the resulting chloroformate with dimethylamine, there is obtained 1,2-dihydro-4,4-dimethyl-9-(N,N-dimethylcarbamyloxy)-7-(3-methyl-2-octyl)-4H-thieno[2,3-c][1]benzopyran.

EXAMPLE 23

1,2-Dihydro-4,4-dimethyl-7-(3-methyl-2-octyl)-9-phosphonyloxy-4H-thieno[2,3-c][1]benzopyran By reacting 1,2-dihydro-4,4-dimethyl-9-hydroxy-7-(3-methyl-2-octyl)-4H-thieno[2,3-c][1]benzopyran with one molar equivalent of phosphorus oxychloride in an inert organic solvent such as toluene, and in the presence of a basic catalyst such as pyridine and reacting the resulting dichlorophosphinate with aqueous potassium carbonate, there is obtained 1,2-dihydro-4,4-dimethyl-7-(3-methyl-2-octyl)-9-phosphonyloxy-4H-thieno[2,3-c][1]benzopyran.

EXAMPLE 24

9-(2-Diethylaminoethoxy)-1,2-dihydro-4,4-dimethyl-7-(3-methyl-2-octyl)-4H-thieno[2,3-c][1]benzopyran 1,2-Dihydro-4,4-dimethyl-9-hydroxy-7-(3-methyl-2-octyl)-4H-thieno[2,3-c][1]benzopyran is reacted with one molar equivalent of sodium ethoxide in a suitable solvent such as absolute ethanol. The solvent is removed on a rotary evaporator and the residue is dried in vacuo. By reacting the sodium derivative of the phenol with an equimolar amount of diethylaminoethyl chloride in benzene, there is obtained 9-(2-diethylaminoethoxy)-1,2-dihydro-4,4-dimethyl-7-(3-methyl-2-octyl)-4H-thieno[2,3-c][1]benzopyran. By methods well known in the art this product is reacted with a suitable acid, such as HCl, to give the corresponding acid addition salt.

EXAMPLE 25

9-[4-(Diethylamino)butyryloxy]-1,2-dihydro-4,4-dimethyl-7-(3-methyl-2-octyl)-4H-thieno[2,3-c][1]benzopyran hydrochloride 0.5 g. (1.39 mmole) of 1,2-dihydro-4,4-dimethyl-9-hydroxy-7-(3-methyl-2-octyl)-4H-thieno[2,3-c][1]benzopyran, 0.31 g. (1.50 mmole; Aldrich Chemical Co.) of dicyclohexylcarbodiimide and 0.272 g. (1.39 mmole) of 4-diethylaminobutyric acid hydrochloride (F. F. Blicke, W. B. Wright, Jr., and M. R. Zienty, J. Amer. Chem. Soc., 63 2488 (1941)) were combined in 30 ml. of methylene chloride and stirred at room temperature for 4 hours. The insoluble by-product of dicyclohexylurea was separated by filtration and the methylene chloride was removed on a rotary evaporator. Attempts to crystallize the material were unsuccessful and 400 mg. (53%) of dark brown residue was obtained. The structure was confirmed by the IR and NMR spectra; and TLC gave $R_f$ 0.5 in 5% MeOH/CHCl$_3$. The acid addition salt may be converted to the free base form by methods well known in the art, and the resulting free base form may then be reacted with another suitable acid to form a different acid addition salt.

EXAMPLE 26

1,3-Dihydro-9-hydroxy-7-(3-methyl-2-octyl)-4-oxo-4H-thieno[3,4-c][1]benzopyran

A.

Methyl-4-oxo-2,3,4,5-tetrahydrothiophene-3-carboxylate

The procedure of Woodward and Eastman (J. Amer. Chem. Soc. 68, 2229 (1946) was followed for the cyclization of 48 g. (0.25 mole) of methyl 3-(methoxycarbonylmethylthio)propionate to give 19.8 g. (50%) of methyl-4-oxo-2,3,4,5-tetrahydrothiophene-3-carboxylate. The IR and NMR spectra indicated the product to be the desired isomer.

B.

1,3-Dihydro-9-hydroxy-7-(3-methyl-2-octyl)-4-octyl)-4-oxo-4H-thieno[3,4-c][1]benzopyran A solution of 20 g. (0.125 mole) of the methyl 4-oxo-2,3,4,5-tetrahydrothiophene-3-carboxylate prepared in A and 32 g. (0.135 mole) of 5-(3-methyl-2-octyl)resorcinol in 200 ml. of absolute ethanol was cooled in an ice-salt bath and saturated with anhydrous hydrogen chloride. The reaction mixture was allowed to stand at room temperature for 72 hours and the solid which formed was removed by filtration. Recrystallization from ethanol gave 16 g. (37%) m.p. 165 –166 C. The structure was confirmed by the IR and NMR spectra.

EXAMPLE 27

1,3-Dihydro-4,4-dimethyl-9-hydroxy-7-(3-methyl-2-octyl)-4H-thieno[3,4-c][1]benzopyran A suspension of 6.0 g. (0.017 mole) of the pyrone of Example 26, part B, in 150 ml. of benzene was added to a Grignard reagent prepared by adding bromomethane to 8.47 g. (0.36 mole) of magnesium turnings in 100 ml. of ether. The mixture was heated at 45°C for 24 hours and then decomposed by the addition of dilute hydrochloric acid. The organic layer was separated, washed with water, dried over sodium sulfate and evaporated to give a gummy residue. This material, as the triol, was dissolved in benzene and refluxed for 3 hours with a few crystals of p-toluenesulfonic acid. The benzene solution was washed, dried and evaporated to give a dark gum which was chromatographed using Florisil (60–100 mesh) and graded ether/petroleum ether solvent mixtures. 2.6 g. (42%) of colorless gum was obtained. The material was shown to be pure by TLC (20% ether/petroleum ether) and exhibited $\lambda_{max}^{EtOH}$ 284 m$\mu$ (log$\epsilon$ 4.157). The IR and NMR spectra were in agreement with the proposed structure.

Anal. Calcd. for $C_{22}H_{32}O_2S$ : C, 73.33; H, 8.91; Found: C, 73.21; H, 8.76

EXAMPLE 28

1,2-Dihydro-10-hydroxy-8-(3-methyl-2-octyl)-5-oxo-4H,5H-thiopyrano[3,4-c][1]benzopyran A solution of 6.4 g (0.027 mole) of 5-(3-methyl-2-octyl)resorcinol of Example 1 and 5.0 g. (0.0266 mole) of ethyl 4-oxo-2,3,5,6-tetrahydro-4H-thiopyran-3-carboxylate (Bennett and Scorah, J. Chem. Soc., 194 (1922)) in 35 ml. of absolute ethanol was cooled in an ice bath while it was saturated with hydrogen chloride. The resulting deep red solution was tightly stoppered and allowed to stand at room temperature for 120 hours. After one day yellow crystalline material had collected on the bottom of the flask. The reaction mixture was warmed gently on the steam bath for 15 minutes, cooled and poured onto a water-ice mixture. The gum-like material that precipitated was extracted with several portions of chloroform. The chloroform solution was washed with aqueous potassium bicarbonate and with water and dried over sodium sulfate. Evaporation of the solvent left 7.5 g. of a light-colored solid. This material was triturated several times with boiling petroleum ether to remove unreacted keto ester. The residue was recrystallized from an ethyl acetate-petroleum ether mixture to give 6.5 g. (68%) of the compound of formula XXXII, m.p. 153°–155°C.

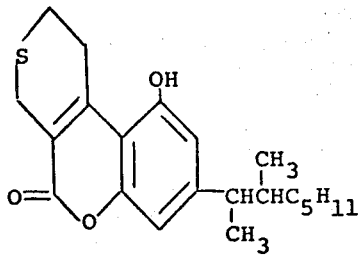

XXXII

The NMR spectrum of this material was consistent with the assigned structure. From another preparation the analytical sample, m.p. 150°–152°C, was obtained after two recrystallizations from ethyl acetate-petroleum ether. It exhibited $\lambda_{max}^{EtOH}$ 310 m$\mu$ (log$\epsilon$ 3.996).

Anal. Calcd. for $C_{21}H_{28}O_3S$: C, 70.00; H, 7.78; S, 8.89; Found: C, 69.99; H, 7.99; S, 8.83

EXAMPLE 29

1,2-Dihydro-5,5-dimethyl-10-hydroxy-8-(3-methyl-2-octyl)-4H,5H-thiopyrano[3,4-c][1]benzopyran A Grignard reagent was prepared in a preflamed apparatus under an atmosphere of nitrogen by bubbling bromomethane into a 250 ml. 3-necked, round-bottomed flask containing 2.03 g. (0.0833 mole) of magnesium in 50 ml. of dry ether. When the magnesium had all reacted, 10 ml. of ether was distilled from the reaction mixture to remove excess bromomethane. A solution of 3 g. (0.00733 mole) of the thiopyrone as prepared in Example 28 was suspended in 30 ml. of dry benzene and 15 ml. of dry ether and was added dropwise to the Grignard solution during a period of 45 minutes. The reaction mixture was refluxed for five days, cooled and poured slowly into a mixture of 75 ml. of saturated ammonium chloride solution and 50 g. of ice. The benzene layer was separated and the aqueous layer was extracted several times with benzene. The combined extracts were washed with water, aqueous potassium bicarbonate solution, again with water, dried over sodium sulfate and then evaporated to give 3.5 g. of brown residue. This residue was dissolved in 150 ml. of dry n-heptane and when the solution was heated to boiling, four drops of 48% hydrobromic acid was added. After heating for 40 minutes, the solution was allowed to stand overnight and was filtered to remove a small amount of precipitate. Evaporation of the filtrate gave 2.6 g. (84%) of crude thiopyran. One gram of this material, purified in two 0.5 g. batches by heating in a sublimation apparatus at 150°C/0.1 mm, gave 200 mg. of a yellow viscous oil of the formula XXXIII

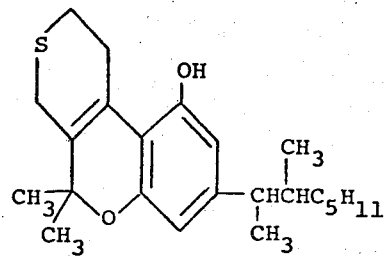

XXXIII

The NMR spectrum of this oil was consistent with the structure of the desired product XXXIII. Thin-layer chromatography (ethyl acetate/hexane, 1:9) showed a major spot ($R_f$ 0.80) and a minor spot ($R_f$ 0.74). The UV spectrum showed $\lambda_{max}^{EtOH}$ 275 m$\mu$ (log$\epsilon$ 3.6).

Anal. Calcd. for $C_{23}H_{34}O_2S$: C, 73.73; H, 9.15; S, 8.54; Found: C, 73.57; H, 9.14; S, 8.76

EXAMPLE 30

1,2-Dihydro-10-hydroxy-8-(3-methyl-2-octyl)-5-oxo-3H,5H-thiopyrano[2,3-c][1]benzopyran A. Methyl 3-oxo-2,3,4,5-tetrahydro-6H-thiopyran-2-carboxylate The procedure of Leonard and Figueras (J. Amer. Chem. Soc. 74, 917 (1952)) was followed for the cyclization of 20 g. of carbomethoxymethyl γ-carbomethoxypropyl sulfide to give 11.1 g. (70%) of methyl 3-oxo-2,3,4,5-tetrahydro-6H-thiopyran-2-carboxylate. The structure was confirmed by IR and NMR spectra.

B.

1,2-Dihydro-10-hydroxy-8-(3-methyl-2-octyl)-5-oxo-3H,5H-thiopyrano[2,3-c][1]benzopyran A solution of 14.2 g. (0.06 mole) of 5-(methyl-2-octyl)resorcinol and 11.1 g. (0.063 mole) of methyl 3-oxo-2,3,4,5-tetrahydro-6H-thiopyran-2-carboxylate in 90 ml. of absolute ethanol was cooled in an ice-salt bath and saturated with anhydrous hydrogen chloride. After standing for 2 days at room temperature, the ethanol was removed on a rotary evaporator. The residue was dissolved in ether, washed with sodium bicarbonate solution and dried over sodium sulfate. Evaporation of the solvent gave 28.0 g. of residue which was chromatographed using Florisil (60–100 mesh) and graded methanol/chloroform solvent mixtures. A total of 10 g. of crude solid was obtained from the 1% methanol/chloroform fractions. The material was recrystallized twice from ethyl acetate/hexane to give 8.5 g. (40%) colorless crystals, m.p. 131°–133°C. The proposed structure was confirmed by IR and NMR spectra.

EXAMPLE 31

1,2-Dihydro-5,5-dimethyl-10-hydroxy-8-(3-methyl-2-octyl)-3H,5H-thiopyrano[2,3-c][1]benzopyran Methylmagnesium bromide was prepared by bubbling bromomethane into a mixture of 7.68 g. (0.32 mole) of magnesium turnings in ether. When all the magnesium had reacted, the solution was refluxed for a short time to remove the excess bromomethane. A solution of 6.96 g. (0.02 mole) of the pyrone (prepared as above) in benzene was added and the reaction mixture was kept at 45°C for 24 hours. The reaction mixture was decomposed with saturated ammonium chloride; the organic layer was separated and the aqueous layer was extracted twice with ether. The organic layers were combined, washed with water, dried and evaporated to give a gummy residue. The IR and NMR spectra indicated the compound to be 5-(3-methyl-2-octyl)-2-(4,5-dihydro-2-(2-hydroxy-2-propyl)-6H-thiopyran-3-yl)resorcinol.

A small quantity of p-toluenesulfonic acid was added to a benzene solution of the above triol and the mixture was heated at reflux for 1½ hours in the presence of nitrogen. The benzene solution was washed with sodium bicarbonate solution, dried over sodium sulfate and evaporated to give a greenish-brown residue.

Chromatography using Florisil (60–100 mesh) and graded ether/petroleum ether solvent mixtures gave 5.2 g. (60%) of a nearly colorless gum. The gum exhibited $\lambda_{max}^{EtOH}$ 305 m$\mu$ (log$\epsilon$ 4.262) and the IR, NMR and UV spectra confirmed the structure as 1,2-dihydro-5,5-dimethyl-10-hydroxy-8-(3-methyl-2-octyl)-3H,5H-thiopyrano[2,3-c][1]benzopyran.

Anal. Calcd. for $C_{23}H_{34}O_2S$: C, 73.73; H, 9.15; S, 8.54; Found: C, 73.55; H, 9.12; S, 8.45

We claim:

1. A compound of the formula

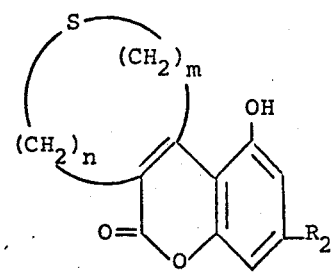

wherein $m$ and $n$ are each 0, 1, 2 or 3 and $m + n$ is 2 or 3 and $R_2$ is alkyl containing from 1 through 20 carbon atoms or cycloalkylloweralkyl in which the cycloalkyl group contains from 3 through 8 ring carbon atoms and the loweralkyl group contains from 1 through 6 carbon atoms.

2. A compound in accordance with claim 1 wherein $m$ is 2, $n$ is 0 and said compound is of the formula

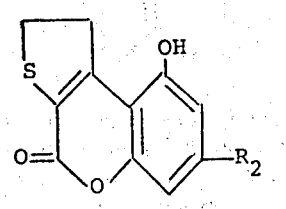

wherein $R_2$ is alkyl containing from 1 through 20 carbon atoms or cycloalkylloweralkyl in which the cycloalkyl group contains from 3 through 8 ring carbon atoms and the loweralkyl group contains from 1 through 6 carbon atoms.

3. A compound in accordance with claim 2 wherein $R_2$ is 3-methyl-2-octyl and said compound is 1,2-dihydro-9-hydroxy-7-(3-methyl-2-octyl)-4-oxo-4H-thieno[2,3-c][1]benzopyran.

4. A compound in accordance with claim 1 wherein $m$ is 1, $n$ is 1 and said compound is of the formula

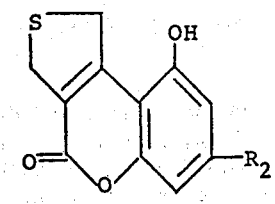

wherein $R_2$ is alkyl containing from 1 through 20 carbon atoms or cycloalkylloweralkyl in which the cycloalkyl group contains from 3 through 8 ring carbon atoms and the loweralkyl group contains from 1 through 6 carbon atoms.

5. A compound in accordance with claim 4 wherein $R_2$ is 3-methyl-2-octyl and said compound is 1,3-dihydro-9-hydroxy-7-(3-methyl-2-octyl)-4-oxo-4H-thieno[3,4-c][1]benzopyran.

6. A compound in accordance with claim 1 wherein $m$ is 0, $n$ is 2 and said compound is of the formula

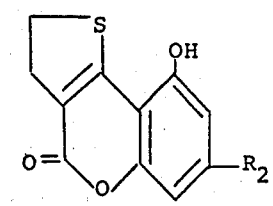

wherein $R_2$ is alkyl containing from 1 through 20 carbon atoms or cycloalkylloweralkyl in which the cycloalkyl group contains from 3 through 8 ring carbon atoms and the loweralkyl group contains from 1 through 6 carbon atoms.

7. A compound in accordance with claim 1 wherein $m$ is 3, $n$ is 0 and the compound is of the formula

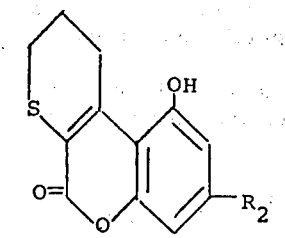

wherein $R_2$ is alkyl containing from 1 through 20 carbon atoms or cycloalkylloweralkyl in which the cycloalkyl group contains from 3 through 8 ring carbon atoms and the loweralkyl group contains from 1 through 6 carbon atoms.

8. A compound in accordance with claim 7 wherein $R_2$ is 3-methyl-2-octyl and said compound is 1,2-dihydro-10-hydroxy-8-(3-methyl-2-octyl)-5-oxo-3H,5H-thiopyrano[2,3-c][1]benzopyran.

9. A compound in accordance with claim 1 wherein $m$ is 2, $n$ is 1 and said compound is of the formula

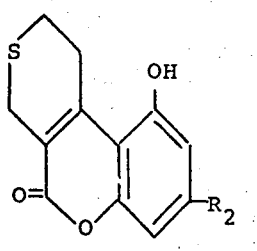

wherein $R_2$ is alkyl containing from 1 through 20 carbon atoms or cycloalkylloweralkyl in which the cycloalkyl group contains from 3 through 8 ring carbon atoms and the loweralkyl group contains from 1 through 6 carbon atoms.

10. A compound in accordance with claim 9 wherein $R_2$ is 3-methyl-2-octyl and said compound is 1,2-dihydro-10-hydroxy-8-(3-methyl-2-octyl)-5-oxo-4H,5H-thiopyrano[3,4-c][1]benzopyran.

11. A compound in adcordance with claim 1 wherein $m$ is 1, $n$ is 2 and said compound is of the formula

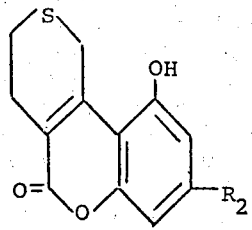

wherein $R_2$ is alkyl containing from 1 through 20 carbon atoms or cycloalkylloweralkyl in which the cycloalkyl group contains from 3 through 8 ring carbon atoms and the loweralkyl group contains from 1 through 6 carbon atoms.

12. A compound in accordance with claim 1 wherein $m$ is 0, $n$ is 3 and said compound is of the formula

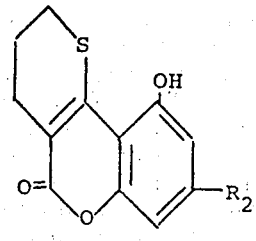

wherein $R_2$ is alkyl containing from 1 through 20 carbon atoms or cycloalkylloweralkyl in which the cycloalkyl group contains from 3 through 8 ring carbon atoms and the loweralkyl group contains from 1 through 6 carbon atoms.

* * * * *